United States Patent [19]

Tuttle

[11] Patent Number: 4,511,570

[45] Date of Patent: Apr. 16, 1985

[54] SENILE DEMENTIA TREATMENT

[75] Inventor: Ronald R. Tuttle, Miami, Fla.

[73] Assignee: Key Pharmaceuticals, Inc., Miami, Fla.

[21] Appl. No.: 479,638

[22] Filed: Mar. 28, 1983

[51] Int. Cl.³ .......................................... A61K 31/485
[52] U.S. Cl. ................................... 514/282; 514/879
[58] Field of Search .......................................... 424/260

[56] References Cited

U.S. PATENT DOCUMENTS 4,454,142  6/1984  Tuttle ................................ 424/260

Primary Examiner—Stanley J. Friedman
Attorney, Agent, or Firm—Wegner & Bretschneider

[57] ABSTRACT

A method is provided for orally treating a patient suffering from senile dementia which comprises the periodic oral delivery of a pharmaceutically effective amount of 6-methylene-6-desoxy-N-cyclopropylmethyl-14-hydroxydihydronormorphone to said patient, whereby the patient tends to reduce his food intake. Also provided is an oral sustained release dosage unit form suitable for treating a patient suffering from obesity which permits a prolonged interval between administration to said patient, said oral dosage unit formulation comprising a plurality of granules which together constitute a pharmaceutically effective amount of 6-methylene-6-desoxy-N-cyclopropylmethyl-14-hydroxydihydronormorphone to provide a sustained action over said prolonged interval, said plurality of granules each comprising a polymeric matrix to permit a substantially even release of said 6-methylene-6-desoxy-N-cyclopropylmethyl-14-hydroxydihydronormorphone to permit the necessary sustained release over the prolonged period of time.

4 Claims, No Drawings

SENILE DEMENTIA TREATMENT

SUMMARY OF THE INVENTION

In accordance with a first aspect of the invention there is provided a method of orally treating a patient suffering from senile dementia which comprises the periodic oral delivery of a pharmaceutically effective amount of 6-methylene-6-desoxy-N-cyclopropylmethyl-14-hydroxydihydronormorphone to said patient to counter the progression of senile dementia in said subject. The periodic oral delivery is at least once per day, but preferably not more than twice per day.

The not more than twice daily regimen is particularly important in the case of a memory loss patient, who may himself forget to take the medication on schedule. The administration of the dose with a twice daily schedule is advantageously timed to coincide with the presence of a friend or relative. For example, the usual sufferer from senile dementia is of an advanced age who may be residing with an adult child, who would be able to observe the actual taking of the mediation to coincide with the regular breakfast and dinner meals, but who would not be available to observe whether the subject is taking the mediation, for example, during the daytime when that adult relative is away at work or occupied with other chores. Accordingly, in accordance with a further aspect of the present invention it is contemplated that to provide an oral sustained release dosage unit form suitable for treating a patient suffering from senile dementia which permits a prolonged interval between administration to said patient, said oral dosage unit formulation comprising a plurality of granules which together constitute a pharmaceutically effective amount of 6-methylene-6-desoxy-N-cyclopropylmethyl-14-hydroxydihydronormorphone over said prolonged interval, said plurality of granules each comprising a polymeric matrix to permit a substantially even release of said 6-methylene-6-desoxy-N-cyclopropylmethyl-14-hydroxydihydronormorphone to permit the necessary sustained release over the prolonged period of time. The oral sustained release dosage form is generally a tablet compressed of said plurality of granules, or a capsule containing these granules.

DETAILED DESCRIPTION OF THE INVENTION

It has recently been proposed that naloxone is useful in the treatment of senile dementia. Thal et al, *New England Journal of Medicine,* 308, 720 (1983); and Reisberg et al, *New England Journal of Medicine,* 308, 721–722 (1983). In accordance with the present invention, an orally suitable formulation is provided that is based upon 6-methylene-6-desoxy-N-cyclopropylmethyl-14-hydroxydihydronormorphone. Recent studies demonstrate that certain drugs may effect a selective loss of choline acetyltransferase in the cortex of patients that suffer from Alzheimer's disease.

The total daily dosage per adult will of course vary dependent upon the weight of the patient, but calculated upon the weight of a normal adult a dosage of from about 10 to about 150 mg per day is contemplated, and still more preferably about 30 to about 70 mg per day. Preferably, a daily dose is preferred which is about 50 mg per day.

A sustained release dosage unit form is provided for 6-methylene-6-desoxy-N-cyclopropylmethyl-14-hydroxydihydronormorphone to release the agent over a prolonged period of at least about eight, and preferably at least about 12 hours, to permit a patient to typically take one oral sustained release dosage form before breakfast, for example, when taking orange juice or other breakfast drink, and just before dinner. In a preferred embodiment, the oral dosage unit form is a tablet, but other sustained release forms are also contemplated, for example, capsules or spanules may also be used. As a preferred oral dosage unit form may be mentioned a plurality of granules each of which contains an essentially uniform distribution of the pharmaceutically active ingredient, the 6-methylene-6-desoxy-N-cyclopropylmethyl-14-hydroxydihydronormorphone, contained in a sustained release vehicle, which sustained release vehicle releases the 6-methylene-6-desoxy-N-cyclopropylmethyl-14-hydroxydihydronormorphone over a prolonged period of time whereby the possibility of infrequent, preferably not more than twice a day, dosing is achieved. As the sustained release vehicle may be mentioned a mixture of cellulosic polymers such as hydroxypropyl methylcellulose typically having a molecular weight of from about 20,000 to about 140,000 which may be advantageously mixed with polyvinylpyrrolidone having a molecular weight of about 20,000 to about 100,000, and preferably about 40,000. When polyvinylpyrrolidone is used it is preferably used in an amount of from about 0.2 to about 0.5 parts per unit of cellulosic polymer.

A total dosage of from about 5 to about 50 mg per oral sustained release dosage unit is contemplated. In a preferred embodiment where the oral sustained release dosage unit is to be delivered on a once per 12 hour basis the total quantity of 6-methylene-6-desoxy-N-cyclopropylmethyl-14-hydroxydihydronormorphone per dosage unit form is from about 15 to about 35 mg, and still more preferably about 25 mg. It is contemplated that the dosage unit formulation include at least about 200 and preferably at least about 400 of the granules per dosage unit, and not more than about 1500 granules per dosage unit formulation. The use of about 600 such granules is contemplated in a preferred embodiment.

When the oral dosage unit formulation is to be in the form of a tablet, the granules are mixed together with typical tableting excipients, for example, about 1% magnesium stearate. In a further variation of the present invention, there may also be included a minor amount, typically not more than about 3% of the total weight, of a flavoring agent. This flavoring agent may be based upon a sweetener which is essentially devoid of significant caloric value. In this variation, there is included in the mixture adding the tableting excipient preferably about 0.2 to about 1% of the tablet weight, be comprised of a sweetener without significant caloric value, for example, saccharine or L-aspartyl-L-phenylalanine.

As an alternative embodiment to the tablet as the oral dosage unit formulation may be mentioned a capsule, which would simply include the necessary plurality of granules that would be released into the gastrointestinal tract upon the dissolution of the capsule.

A rectal suppository is also contemplated as an alternate sustained release vehicle, in which case a wax vehicle is contemplated for the sustained release of the 6-methylene-6-desoxy-N-cyclopropylmethyl-14-hydroxydihydronormorphone over the desired prolonged period of time.

While 6-methylene-6-desoxy-N-cyclopropylmethyl-14-hydroxydihydronormorphone has been referred to as the active ingredient of the present invention, it is contemplated that any pharmaceutically acceptable salt form may be used, and it is preferred that the hydrochloride be used in formulations unless otherwise specified. Other forms derived from 6-methylene-6-desoxy-N-cyclopropylmethyl-14-hydroxydihydronormorphone may also be used and are specifically considered to be within the scope of the invention.

The following examples serve to illustrate the invention:

EXAMPLE I

Mixed together are 45 gm 6-methylene-6-desoxy-N-cyclopropylmethyl-14-hydroxydihydronormorphone; 130 gm polyvinylpyrrolidone (mw 40,000); and 240 gm hydroxypropylmethylcellulose (mw=120,000, Methocel K15M, Dow Chemical). The blend which results from this mixture is granulated with 160 ml deionized water to produce granules which are then dried at a temperature of 50° C., followed by grinding. The sufficiently small granules which are obtained by passing the mixture of granules through a 14 mesh screen are then lubricated with 5 mg magnesium stearate, and tablets having a total weight of 500 mg are thereafter compressed from this mixture.

EXAMPLE II

To obtain a sweetened sustained release dosage unit form, one follows the procedure set forth in the immediately preceding example I, but adds 4 mg L-aspartyl-L-phenylalanine together with the addition of the 5 mg magnesium stearate, a sweetened tablet is obtained without significant caloric value.

EXAMPLE III

To provide sufficient 6-methylene-6-desoxy-N-cyclopropylmethyl-14-hydroxydihydronormorphone to a patient suffering from senile dementia, a tablet of Example I is administered at breakfast and again at dinnertime on a regular basis, to provide a sustained release of 6-methylene-6-desoxy-N-cyclopropylmethyl-14-hydroxydihydronormorphone.

What is claimed is:

1. A method of orally treating a patient suffering from senile dementia which comprises the periodic oral delivery of a pharmaceutically effective amount of 6-methylene-6-desoxy-N-cyclopropylmethyl-14-hydroxydihydronormorphone to said patient to counter the progression of senile dementia in said subject.

2. A method of claim 1 wherein said periodic oral delivery is at least once per day.

3. A method of claim 2 wherein said periodic oral delivery is at least twice per day.

4. A method of claim 1 wherein said pharmaceutically acceptable amount is from about 10 to about 150 mg per day based upon a normal adult body weight.

* * * * *

UNITED STATES PATENT AND TRADEMARK OFFICE
CERTIFICATE OF CORRECTION

PATENT NO. : 4,511,570

DATED : April 16, 1985

INVENTOR(S) : Ronald R. Tuttle

It is certified that error appears in the above-identified patent and that said Letters Patent is hereby corrected as shown below:

In the Abstract:
Lines 5-6, delete ", whereby the patient tends to reduce his food intake" and substitute therefor -- to counter the progression of senile dementia in said patient --, Lines 8-9, delete "obesity" and substitute therefor -- senile dementia --, Column 1, line 22 and line 25, "mediation" should read -- medication --.

Column 2, lines 53-57, delete sentence beginning "In this variation" and ending "with L-aspartyl-L-phenylalanine." and substitute therefor -- In this variation, the flavoring agent is added to the mixture preferably in an amount of about 0.2 to about 1% of the tablet weight. Representative sweeteners without significant caloric value are, for example, saccharine or L-asparty-L-phenylalanine. --

Signed and Sealed this

Twenty-fourth Day of December 1985

[SEAL]

Attest:

DONALD J. QUIGG

Attesting Officer

Commissioner of Patents and Trademarks